United States Patent
Slaugh et al.

(10) Patent No.: US 6,576,806 B1
(45) Date of Patent: *Jun. 10, 2003

(54) PROCESS FOR SEPARATING $C_2$-$C_3$ OLEFINS FROM INDUSTRIAL GASES

(75) Inventors: Lynn Henry Slaugh, Cypress, TX (US); Howard Lam-Ho Fong, Sugar Land, TX (US); Laurent Alain Fenouil, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/467,806

(22) Filed: Dec. 20, 1999

(51) Int. Cl.⁷ .............................................. C07C 7/152
(52) U.S. Cl. ........................ 585/867; 585/809; 585/833; 585/866
(58) Field of Search .............................. 585/867, 833, 585/809, 866

(56) References Cited

U.S. PATENT DOCUMENTS

| | | | | |
|---|---|---|---|---|
| 2,775,633 | A | 12/1956 | Fenske et al. ............... | 260/677 |
| 2,953,611 | A | 9/1960 | Spengler ..................... | 260/677 |
| 3,306,946 | A | 2/1967 | Snyder et al. .............. | 260/677 |
| 3,444,261 | A | 5/1969 | Caprioli et al. ............. | 260/683 |
| 3,534,116 | A | 10/1970 | Fuller ......................... | 260/674 |
| 3,864,420 | A | 2/1975 | Dombro ................. | 260/677 A |
| 4,710,273 | A | 12/1987 | Okamoto ..................... | 203/29 |
| 4,915,794 | A | 4/1990 | Slaugh et al. ................. | 203/29 |
| 4,946,560 | A | 8/1990 | Slaugh et al. ................. | 203/38 |
| 5,012,034 | A | 4/1991 | Weingaertner et al. ..... | 585/806 |
| 5,936,136 | A | 8/1999 | Slaugh et al. ............... | 585/867 |
| 5,942,656 | A | 8/1999 | Slaugh et al. ............... | 585/864 |
| 6,018,089 | A | * 1/2000 | Slaugh et al. ............... | 585/867 |
| 6,175,050 | B1 | * 1/2001 | Slaugh et al. ............... | 585/867 |
| 6,184,431 | B1 | * 2/2001 | Slaugh et al. ............... | 585/867 |
| 6,211,423 | B1 | * 4/2001 | Slaugh et al. ............... | 585/867 |
| 6,271,434 | B1 | * 8/2001 | Slaugh et al. ............... | 585/867 |

FOREIGN PATENT DOCUMENTS

WO    WO 00/68171    11/2000

OTHER PUBLICATIONS

International Search Report of Mar. 21, 2001.
U.S. patent application Ser. No. 08/987,554, Slaugh et al., filed Dec. 9, 1997.
U.S. patent application Ser. No. 08/876,822, Slaugh et al., filed Jun. 16, 1997.
U.S. patent application Ser. No. 08/987,553, Slaugh et al., filed Dec. 9, 1997.

* cited by examiner

*Primary Examiner*—Walter D. Griffin

(57) ABSTRACT

A process for treating a feedstock comprising olefins having an average carbon number ranging from 2–3.5, and non-olefinic compounds, said process comprising the following steps:

a) contacting gaseous feedstock with a linear polyaromatic compound in a reaction zone under conditions effective to form a reaction mixture comprising linear polyaromatic compound-olefin adducts and unreacted gaseous feedstock;

b) separating the olefin adducts from the unreacted gaseous feedstock; and c) dissociating the olefin adducts to form linear polyaromatic compounds and an olefin enriched composition comprising ethylene, propylene, or mixtures thereof;

whereby the concentration of at least one of the olefins in said olefin enriched composition is enriched over the concentration of said at least one olefin present in the feedstock.

145 Claims, No Drawings

US 6,576,806 B1

PROCESS FOR SEPARATING C$_2$-C$_3$ OLEFINS FROM INDUSTRIAL GASES

FIELD OF THE INVENTION

This invention relates to a process for separating C$_2$–C$_3$ olefins from industrial gases.

BACKGROUND OF THE INVENTION

Many industrial processes produce olefin streams within the average carbon number range of C$_2$–C$_3$. The feedstock may be generated by commercial processes such as the olefinic (ethylene) products of hydrocarbon pyrolysis furnaces. Such hydrocarbon pyrolysis furnaces are typically fed by natural gas liquids, which contain significant amounts of ethane, propane, butane, or gasoline, or fed by naphtha or gas oil. Also the term "steam cracker for production of olefins" is used. In some instances, operators do actually feed olefins to the cracking furnaces such as where they don't have a market for C3, C4, C5 olefins, so the term "olefins steam cracker" could be misunderstood, olefins normally not being a cracker feedstock. Other processes which generate feedstocks containing olefins include streams produced from the light ends (C$_4$ or less) of any refinery thermal cracker using a vacuum flasher bottoms as the feed; a stream from the light ends (C$_4$ or less) of any coker using a vacuum flasher bottoms as the feed; any one of the product streams from a fluidized catalytic cracking, (FCC) unit's gas plant receiving the C$_4$ or less cuts from a crude distillation column; the overhead of a cat cracking unit; or the C$_4$ or less cut of a fractionation column fed by the product of a FCC Unit.

In many of these process, olefins are separated from impurities and by-products, such as saturated hydrocarbons, sulfur compounds, carbon oxides, and nitrogen containing compounds through costly cryogenic distillation, due to operating the process with expensive refrigeration units. Since the industrial C2–C3 streams are gaseous at room temperature, these streams are first cooled to liquify the ingredients followed by subjecting the liquid stream to a distillation process for separating the olefins from the liquid mixture. Another process to separate impurities, such as acetylenes, from ethylene streams is a solvent extraction. Solvent extraction, however, is not effective for separating olefins from saturated hydrocarbons. It would be desirable to separate out olefins from a wide variety of impurities and by-products, such as saturated hydrocarbons, carbon oxides, and sulfur and nitrogen bearing compounds, present in industrial streams containing olefins in the C$_2$–C$_4$ range, and which does not require the use of cryogenic units to conduct the separation.

U.S. Pat. Nos. 4,946,560, 5,936,136, and 5,942,656 describe processes for the separation of internal olefins from alpha olefins, and linear alpha olefins from 2-branched and/or 3-branched alpha olefins, by contacting a feedstock with an adducting compound such as anthracene or benzanthracene to form an olefin adduct, separating the adduct from the feedstock, dissociating the olefin adduct through heat to produce anthracene and an olefin composition enriched in alpha olefin, and separating out the anthracene from the alpha olefin. This reference does not suggest the desirability or the capability of anthracene to separate C$_2$–C$_3$ olefins contained in industrial streams from a gaseous mixture of C$_2$–C$_3$ olefins, saturated hydrocarbons, carbon oxides, sulfur bearing compounds, and nitrogen bearing compounds.

SUMMARY OF THE INVENTION

This invention relates to a process for treating a feedstock comprising olefins having an average carbon number ranging from, 2–3.5, and non-olefinic compounds, said process comprising the following steps:

a) contacting gaseous feedstock with a linear polyaromatic compound in a reaction zone under conditions effective to form a reaction mixture comprising linear polyaromatic compound-olefin adducts and unreacted gaseous feedstock;

b) separating the olefin adducts from the unreacted gaseous feedstock; and c) dissociating the olefin adducts to form linear polyaromatic compounds and an olefin enriched composition comprising ethylene, propylene, or mixtures thereof;

whereby the concentration of at least one of the olefins in said olefin enriched composition is enriched over the concentration of the corresponding olefin in the feedstock.

DETAILED DESCRIPTION OF THE INVENTION

As used throughout this specification and in the claims, the term "comprising" means "at least," such that other unmentioned elements, ingredients, or species are not excluded from the scope of invention.

The feedstock to be treated comprises at least olefins and non-olefinic compounds, wherein the olefins have an average carbon number ranging from 2–3.5, based on a weighted average of moles of olefins present in the feedstock. An olefin means any compound containing at least one carbon-carbon double bond. Except for ethylene and propylene, other olefins present in the feedstock may be linear or branched. Examples of olefins which are present in the feedstock include at least one of ethylene, proplyene, or mixtures thereof or mixtures with other olefins such as butylene and/or pentenes.

The class of non-olefinic compounds generally includes saturated hydrocarbons. Saturated hydrocarbon include paraffins, and may also include other molecules such as cycloparaffins, which may be present in trace quantities. Other non-olefinic compounds typically present in the feedstock include methane, ethane, carbon dioxide, carbon monoxide, hydrogen, and sulfur and/or nitrogen bearing compounds. Examples of sulfur bearing compounds are $H_2S$, alkyl mercaptans, $CS_2$, and COS. Examples of nitrogen bearing compounds include ammonia, nitrogen, and amines.

The feedstock may be generated by commercial processes such as the product of an olefins (e.g. ethylene) pyrolysis furnaces; an olefins steam cracker; a stream from the light ends (mixtures of C$_4$ hydrocarbons or less) of any refinery thermal cracker using a vacuum flasher bottoms as the feed; a stream from the light ends (mixtures of C$_4$ hydrocarbons or less) of any coker using a vacuum flasher bottoms as the feed; any one of the product streams from a cat cracking gas plant receiving the mixture of C$_4$ hydrocarbons or less cuts from a crude distillation column; the overhead of a cat cracking unit, and/or a catalyst reforming unit; any one of the products from the bottoms of a hydrotreater for removing sulfur compounds; the light butane overhead from a crude distillation column; the mixture of C$_4$ hydrocarbons or less cut of a fractionation column fed by the product of a cat cracker, or derived by removal of light ends (C$_1$–C$_4$) in a Fisher-Tropsch product stream.

In one embodiment, the feedstock is a stream used to feed a C$_2$ splitter fractionation column where ethylene is separated from ethane. The feedstock to a C$_2$ splitter is derived from the product recovery and purification section of an olefins plant and originates in the radiant zone of the pyrolysis furnaces in the plant where feedstock pyrolysis takes place. Generally, the pyrolysis gases from the radiant zone of the ethylene furnace are separated first in a fractionator into gasoline and lighter fractions as an overhead and heavier than gasoline compounds as the bottoms in a fractionator. The overhead gases are compressed and cooled to form liquids and fed to a de-methanizer system to remove hydrogen and methane as an overhead. The remaining compounds from the bottoms of the de-methanizer are fed to a de-ethanizer to remove and isolate $C_2$ compounds as an overhead for feedstock to the C2 splitter fractionation column which would be replaced by this invention. Other separation systems may have equipment arranged in a different sequence, or with different or additional equipment. In this embodiment, however, regardless of the separation system employed, the feedstock used for the separation system according to the invention is derived from an ethylene pyrolysis furnace which has been subjected to one or more separations to concentrate a stream containing $C_2$ compounds, primarily ethylene and ethane. Most of the $C_2$ feedstock streams contain at least 90 wt. % ethane and ethylene, and even at least 95 wt. % ethane and ethylene. Some of these streams contain at least 98 wt. % ethane and ethylene.

In another embodiment, the feedstock is a stream used to feed a $C_3$ splitter fractionation column where propylene is separated from propane. The feedstock to a $C_3$ splitter is derived from the product recovery and purification section of an olefins plant or a FCC Unit as the overhead stream of a depropanizer. Other product recovery and purifications systems may have equipment arranged in a different sequence such that the $C_3$ stream is not the overhead stream of a depropanizer. In this embodiment, however, regardless of the separation system employed, the feedstock used for the separation system according to the invention is derived from an hydrocarbon pyrolysis furnace or an FCC process which has been subjected to one or more separations to concentrate a stream containing $C_3$ compounds, primarily propylene and propane. The process of the invention is suitable to upgrade a $C_3$ stream at a refinery by the separation techniques described below to a chemical (generally containing 92–95 wt % propylene) or polymer grade (containing at least 99.5 wt. % propylene), or to process a refinery grade propylene stream (containing about 60–80 wt. % propylene) off-site through the separation processes described below to a chemical grade or polymer grade propylene stream, or to process the $C_3$ product stream from an steam cracker to produce either a chemical or polymer grade propylene stream.

The feedstock used in the invention has an average olefin carbon number ranging from 2–3.5, preferably from 2–3, inclusive. The feedstock used in the invention contains at least one of ethylene, propylene, or mixtures thereof. In another embodiment, the feedstock comprises ethylene, ethane, hydrogen, and carbon dioxide. In yet another embodiment, the feedstock comprises methane, ethane, ethylene, propylene, carbon dioxide, carbon monoxide, hydrogen, and sulfur and/or nitrogen bearing compounds.

The amount of each ingredient varies widely depending upon the source of the feedstock. In one embodiment, the amount of any one of ethylene and propylene are independently at least 5% by volume, preferably at least 10% by volume. In another embodiment, the feedstock comprises, by volume percentage based on the volume of the feedstock, 5–35% ethylene, 0.0–20% and preferably 1% to 20% propylene, 0.0 to 25% and typically 0.1–25% carbon dioxide, 0.0% to 10% and typically 0.5–10% carbon monoxide, 0.0 to 40% and typically 5–40% hydrogen, and from 0.0% to 4% and typically 0.0005–1% sulfur bearing compounds. In yet another embodiment, the volume percentage of the ingredients in the feedstock comprises from 20–60% methane, 10–30% ethane, 5–35% ethylene, 0.5–20% propylene, 0.1–25% carbon dioxide, 0.5–10% carbon monoxide, 5–40% hydrogen, and from 0.0005–1% sulfur bearing compounds.

The linear polyaromatic compound is utilized in the instant process to form the adduct with the olefins in the feedstock. As used herein, "linear polyaromatic compound" refers to a linear polyaromatic compound having at least three fused aromatic rings, which may be unsubstituted or substituted and possess similar adducting properties as the unsubstituted molecule, and mixtures thereof. The linearity should extend to all three of the fused rings if a three fused ring compound is used and to at least four consecutively fused cyclic rings if a four or more fused ring compound is used. The linear polyaromatic compound also refers to mixtures of compounds containing as one of their ingredients the linear polyaromatic compound, including but not limited to coal tars, anthracene oil, and any crude mixtures containing cuts separated from naphthalene. The linear polyaromatic compound also includes aromatic molecules linked together by a bridging group, such as a-hydrocarbon chain, an ether linkage, or a ketone group containing chain so long as at least three fused rings are present in a linear arrangement; as well as those containing a heteroatom which do not interfere in the separation of olefins from saturated hydrocarbons.

Non-limiting examples of the linear polyaromatic compound include anthracene, 2,3-benzanthracene, pentacene, and hexacene. Suitable examples of substituents on substituted linear polyaromatic compounds include, but are not limited to, lower alkyl, e.g., methyl, ethyl, butyl, isopropyl; halo, e.g., chloro, bromo, fluoro; nitro; sulfato; sulfonyloxy; carboxyl; acetyl; carbo-lower-alkoxy, e.g., carbomethoxy, carbethoxy; amino; mono- and di-lower-alkylamino, e.g., methylamino, dimethylamino, methylethylamino; amido; hydroxy; cyano; lower-alkoxy, e.g., methoxy, ethoxy; lower-alkyanoyloxy, e.g., acteoxy; monocyclic aryls, e.g., phenyl, xylyl, toluyl, benzyl, etc. The particular substituent size, their number, and their location, should be selected so that they are relatively inert under the reaction conditions and not so large as to block the formation of the Diels-Alder adduct. Suitable substituted linear polyaromatic compounds can be determined by routine experimentation. Examples of suitable linear polyaromatic compounds include 9,10-dimethylanthracene, 9,10-dichloroanthracene, 9-methylanthracene, 9-acetylanthracene, 9-(methylaminomethyl)anthracene, 2-choloranthracene, 2-ethyl-9,10-dimethoxyanthracene, anthrarobin, and 9-anthryl trifluoromethyl ketone. The preferred linear polyaromatic compounds are anthracene and 2,3-benzanthracene. In another preferred embodiment, the linear polyaromatic compound comprises anthracene having a purity of 75% or more anthracene. The selectivity of the linear polyaromatic compound toward the olefins in the feedstock of 80% or more, preferably 90% or more, more preferably 95% or more, and most preferably 98% or more, and even 99% or more.

The conversion of the olefins in the feedstock should be sufficiently high to economically justify removal of the olefins from the feedstock. In one embodiment, at least 30%, more preferably at least 40%, of the olefins in the feedstock are converted, depending upon the desired residence time and operational temperatures and pressure.

In a first reaction zone in step a), the feedstock composition having an average olefin carbon number ranging from 2–3.5 is contacted with a linear polyaromatic compound. The resulting products of the reaction are Diels-Alder adducts. Thus, there is provided an adduct of a linear polyaromatic compound and ethylene in one embodiment. In another embodiment, there is provided an adduct of a linear polyaromatic compound and propylene. In each of these embodiments, the preferred linear polyaromatic compound is anthracene, although any of the above identified linear polyaromatic compounds can be used.

The Diels-Alder adduct forming reaction is carried out in a conventional fashion. Examples of suitable equipment in which the reactions are carried out include a continuously stirred tank reactor, configured as a single unit, in parallel, or in series, wherein feedstock or an portion of the olefin composition, and linear polyaromatic compound, are added continuously to a stirred tank to form a liquid reaction mixture under heat, and the reaction mixture is continuously withdrawn from the stirred tank. Alternatively, the reaction may be carried out in a plug flow reactor or a series of plug flow reactors, a bubble column, or in a batch reactor.

The reactions can be carried out by reacting a gaseous feedstock (gaseous under adducting reaction conditions) with the linear polyaromatic compound in the liquid or gaseous phase. In a gas-gas phase, the system pressure should be lowered to sub-atmospheric pressure to volatize the linear polyaromatic compound at a temperature sufficiently low to maintain a stable adduct. In a preferred embodiment, the reaction is carried out by contacting the feedstream in a gaseous phase at reaction conditions with a liquid phase linear polyaromatic compound. In this preferred embodiment, the gaseous feedstock may react to form the adduct upon contact with the liquid linear polyaromatic compound, or the gaseous feedstock may first dissolve into the liquid linear polyaromatic compound followed by formation of the adduct, or both reactions may occur simultaneously.

The method of contact is not limited. Examples of contact include spraying the linear polyaromatic compound into a continuous phase of the gaseous feedstock, or bubbling a gaseous feedstream through a continuous phase of liquid linear polyaromatic compound.

The adducting forming reactions are typically carried out over a range of temperatures depending upon the pressure. Examples of suitable temperatures in this embodiment range from about 150° to about 375° C., more preferably from about 230° to about 320° C., and most preferably from about 240° to about 310° C. In general, the adducting reaction can be carried out under any pressure, but it is preferred to conduct the reaction at elevated pressure to increase the reaction rate. Preferred system pressures range from 50 psig to 1000 psig, and more preferably from 200 to 350 psig.

In the mixed liquid linear polyaromatic compound/olefin gas phase embodiment, the reactor system temperature/pressure is within a range which maintains the linear polyaromatic compound in liquid state without liquifying incoming feedstock in the gas phase and without dissociating the adducts as formed or preventing their formation. Preferred reactor temperatures range from 200–300° C., more preferably from 250–280° C. The reactor system pressure in this embodiment ranges from 0.0 psig to 1000 psig, more preferably from 50 to 500 psig.

The residence time is for a time sufficient to adduct the desired amount of linear polyaromatic compound with the olefin. The optimal time will be the shortest time to attain the target conversion of olefins at the designed reaction temperature and pressure.

An inert solvent can be utilized to dissolve the feedstock olefins or the linear polyaromatic compound or both in each of the adducting reactors. Preferred solvents are the hydrocarbon solvents which are liquid at reaction temperatures and in which the olefins, linear polyaromatic compound and olefin-linear polyaromatic compound adducts are soluble. Illustrative examples of useful solvents include the alkanes such as pentane, iso-pentane, hexane, heptane, octane, nonane, and the like; cycloalkanes such as cyclopentane, cyclohexane, and the like; and aromatics such as benzene, toluene, ethylbenzene, diethylbenzene, and the like. The amount of solvent to be employed can vary over a wide range without a deleterious effect on the reaction.

Preferably, the adducting reactions are carried out in the absence of a solvent, thereby improving the rate of reaction and avoiding the need for additional equipment and process steps for separating the solvent.

After formation of the linear polyaromatic compound-olefin adduct in step a), the adduct stream (optionally and generally including unreacted liquid linear polyaromatic compound) is separated from the unreacted gaseous feedstock in a step b). Step a) and step b) may be, and typically will be, carried out in the same reaction vessel used to conduct the adducting reaction. Further, step b) may be, and typically will be, carried out simultaneously with step a) as the adduct is forming. For example, in a bubble column, as the gaseous feedstock is contacted with a continuous phase of liquid linear polyaromatic compound, adducts of linear polyaromatic compound-olefins are formed while the unreacted gaseous feed continues up through the liquid phase and is removed as a gaseous overhead. The adducts and liquid linear polyaromatic compound are simultaneously removed as the unreacted gases are taken at the overhead. In a spray process, the liquid linear polyaromatic compound may be sprayed into a gaseous feedstream, thereby simultaneously forming the adduct, which along with unreacted linear polyaromatic compound, is removed from any unreacted gaseous feedstock which is removed as an overhead.

The recovery of the linear polyaromatic compound-olefin adducts is determined by the molar ratio of linear polyaromatic compound to olefins, the adducting residence time, the temperature within the reactor vessel, and most importantly, the residence time (rate of separation) of the reaction mixture in the reactor vessel. To obtain a large olefin composition recovery, a high linear polyaromatic compound to olefin molar ratio, e.g., >100, and long residence times to ensure complete adduction.

In the next step of the process, the removed linear polyaromatic compound-olefin adduct stream is dissociated in step c) in a dissociation zone to form linear polyaromatic compounds and an olefin enriched composition. The dissociation process can be accomplished by feeding the adducted olefin stream to a dissociation vessel where the adducted olefin stream is heated and pyrolyzed at a temperature ranging from about 200° to about 500° C., preferably from about 300° to about 350° C., for a time sufficient to dissociate the adducts, thereby releasing the olefin gases from the liquid phase linear polyaromatic compounds. The dissociation temperature can be further reduced below 200° C. by drawing a vacuum on the dissociation vessel. The pyrolysis frees the olefins from the linear polyaromatic compound. One or more dissociation vessels may be used in series to conduct the dissociation.

In an optional but preferable step d), trace or small quantities of linear polyaromatic compound entrained in the released olefin enriched composition may be removed by adsorption with cold linear polyaromatic compound or by scrubbing the gaseous olefin enriched composition with any other appropriate sorbents. Optionally, trace or small quantities of linear polyaromatic compound entrained in the released olefin enriched composition may be removed by simply cooling the gaseous olefin enriched composition, or by flash distillation, thereby removing the olefins from the linear polyaromatic compound.

The linear polyaromatic compounds may be recycled back to the adducting reaction zone or to a mixing zone wherein the linear polyaromatic compound recycle and some fresh linear polyaromatic compound, along with optional feedstock, are premixed prior to entering the adduct reaction zone.

The olefin enriched composition is enriched in the concentration of olefins over the concentration of olefins in the feedstock.

For purposes of measuring the % enrichment of a species in a stream, the concentration of the species or series of species in the predecessor or feedstock stream is subtracted from the concentration of species or series of species in question contained in the product stream, the difference then divided by the concentration of those same species present in the predecessor feedstock stream and multiplied by 100.

In another embodiment of the invention, the concentration of saturated hydrocarbons in the olefin enriched composition is reduced through the process of the invention in only one pass by at least 80%, preferably by at least 90%, more preferably by at least 95% over the concentration of saturated hydrocarbon in the feedstock, and most preferably by.98% or more.

The concentration of olefins in the olefin enriched composition is enriched over the concentration of olefins in the feedstock. The degree of olefin enrichment varies inversely with the concentration of olefins present in the feedstock. In a preferred aspect of this embodiment, the concentration of olefins in the olefin enriched composition is enriched by at least 40%, preferably by at least 60%.

The resulting olefin enriched composition may be used as a feedstock for the manufacture of higher olefins in the C4–C100 range, polyethylene, polypropylene, propylene oxide and derivatives such as propylene glycol, normal butyl alcohol, ethylene oxide and derivatives such as ethylene glycol, ethylbenzene, cumene, isopropyl alcohol, propanol, ethanol, epichlorohydrin, acetone and its derivatives such as MIBK, oligomerization products using a Dimersol™ process or a Polygas™ process, and in any other process which employs ethylene and/or propylene as a feedstock material.

The following examples illustrate an embodiment of the invention and are not intended to limit the scope thereof.

EXAMPLE I

To illustrate the concept of the invention, a gas mixture simulating those available from refinery and chemical operations was used as feedstock. In each of the examples, the concentration of feedstock ingredients and the product ingredients was measured by gas chromatography.

The feedstock composition, in volume %, consisted of carbon dioxide 16.3%, carbon monoxide 5.3%, hydrogen 12.9%, ethylene 29.8%, propylene 10.6%, ethane 20.0%, and propane 5.1%.

About 0.1 moles of anthracene having a 99% purity was placed in an autoclave which was then sealed and purged with the feed gas. The autoclave was heated to reaction temperature and feed gas was introduced through a port at the top of the autoclave to the desired pressure as set forth in Table 1, after which the autoclave contents were stirred and heated. Periodically during the course of the experiment, as the ethylene and propylene reacted with the anthracene to form Diels-Alder adducts; the autoclave was vented and repressured with fresh feed gas.

The crude olefin anthracene adduct product from the above reaction was transferred to a glass flask and heated at 240–250° C. for 0.5–1.5 hours. As the olefin-anthracene adduct dissociated to recyclable anthracene and product olefins, a small stream of pure nitrogen was passed through the flask to carry the olefins to a collection vessel. With the exception of the deliberately introduced nitrogen, the final product consisted entirely of ethylene and propylene. All other undesirable components of the gas feed (carbon dioxide, carbon monoxide, hydrogen, ethane and propane) had been completely removed from the desired ethylene and propylene product. The results of a series of experiments are listed in Table I.

TABLE I

| EXP. NO. | FEED GAS[a] PRESSURE PSIG | TEMP ° C. | TIME, HRS | CONVERSION OF ANTHRACENE TO ANTRACENE ADDUCTS, % | COMPOSITION OF GAS FROM ADDUCT DISSOCIATION, VOLUME % | | |
|---|---|---|---|---|---|---|---|
| | | | | | ETHYLENE | PROPYLENE | OTHER |
| 1 | 300 | 255 | 6 | 57.7 | 75.0 | 25.0 | 0 |
| 2 | 300 | 280 | 6 | 69.6 | 78.5 | 21.5 | 0 |
| 3 | 300 | 280 | 2 | 43.9 | 73.0 | 27.0 | 0 |
| 4 | 90 | 280 | 6 | 21.4 | 78.8 | 21.2 | 0 |
| 5 | 300 | 280 | 14 | 72.1 | 86.0 | 14.0 | TRACE |
| 6 | 300 | 300 | 2 | 36.4 | 79.7 | 20.3 | 0 |
| 7 | 90 | 300 | 6 | 18.2 | 85.0 | 15.0 | 0 |

[a]Feed gas pressure is equivalent in this case to the system reactor pressure.

The results indicate that the olefin concentration by volume % went from 40.4% to 100%, resulting in a 147% enrichment of olefins in the olefin enriched composition. The concentration of olefins in the olefin enriched composition was about 100%.

The results also indicate that the conversion of anthracene to anthracene adducts was enhanced at higher system pressure, higher reaction temperature, and longer residence time. The pressure on the feedstock was a significantly large influence on the percentage conversion.

EXAMPLE II

To further illustrate the concept of the invention, a gas mixture containing some 1-butene as well as ethylene and propylene was used as feed. The average carbon number of olefins was about 2.56. The feed composition in volume % comprised carbon dioxide 15.1%, carbon monoxide 4.9%, hydrogen 11.9%, ethylene 27.5%, propylene 9.8%, 1-butene 7.7%, ethane 18.4%, and propane 4.7%.

The experimental procedures for this experiment were the same as given in Example I. All undesired components of the feed were removed by the process, and a product comprised of ethylene, propylene and 1-butene was obtained, as set forth in Table II.

EXAMPLE IV

A low-value, waste gas from a commercial olefin pyrolysis (OP) unit was similarly treated with anthracene to recover ethylene and propylene from the crude stream containing considerable undesired chemicals. 0.1 mole of 99% purity anthracene in a stirred autoclave was heated at 255° C. for six hours while being exposed to 200–300 psig of the plant off-gas. The resultant crude anthracene-olefin reaction product mixture consisted of 85% unreacted

TABLE II

| EXP. NO. | FEED GAS[a] PRESSURE, PSIG | TEMP ° C. | TIME, HRS | CONVERSION OF ANTHRACENE TO OLEFIN ADDUCT, % | COMPOSITION OF GAS FROM ADDUCT DISSOCIATION, VOLUME % | | | |
|---|---|---|---|---|---|---|---|---|
| | | | | | ETHYLENE | PROPYLENE | 1-BUTENE | OTHER |
| 8 | 325 | 280 | 6 | 37.3 | 71.7 | 21.2 | 7.1 | 0 |

[a]Feed gas pressure was about the same as the system pressure.

The results indicate that the olefin concentration in the olefin enriched composition was enriched by increasing from 45.2% to 100%, for a degree of enrichment of 121%.

EXAMPLE III

Several substituted anthracenes were tested to determine their suitability for recovery at ethylene and propylene from crude gas mixtures. The same procedure as given in Example I was employed, except 25–30 g. of toluene solvent was added to the autoclave. The amount of substituted anthracene employed was 0.01 moles. The gaseous feedstock composition, in volume %, comprised carbon dioxide 16.3%, carbon monoxide 5.3%, hydrogen 12.9%, ethylene 29.8%, propylene 10.6%, ethane 20.0%, and propane 5.1%. The autoclave pressure at reaction temperature was a constant 300 psig.

As can be seen from the tabulated results of Table III, substituted anthracenes are effective for separating valuable ethylene and propylene from the undesired gas components, such as carbon dioxide, carbon monoxide, hydrogen, and saturated hydrocarbons.

anthracene, 13% anthracene-ethylene adduct and 2% anthracene-propylene adduct. This crude product was transferred to a glass flash and heated to dissociate the adducts, in the same manner as Example I. The compositions of the feed gas and the final purified gas product are given in Table IV. This experiment clearly demonstrates that ethylene and propylene can be effectively recovered in high purity.

TABLE IV

| | FEED GAS, VOL. % | PRODUCT GAS, VOL. % |
|---|---|---|
| METHANE | 44.1 | 0 |
| ETHANE | 17.1 | 0 |
| PROPANE | 0.9 | 0 |
| ISOBUTANE | 0.3 | 0 |
| ETHYLENE | 11.9 | 85.3 |
| PROPYLENE | 2.3 | 14.7 |
| CARBON DIOXIDE | 0.9 | 0 |
| CARBON MONOXIDE | 2.1 | 0 |
| HYDROGEN | 20.4 | 0 |
| SULFUR COMPOUNDS[a] | 0.004 | 0 |

[a]Carbon disulfide, carbonyl sulfide, ethyl mercaptan, hydrogen sulfide and methyl mercaptan.

TABLE III

| EXP. NO. | TEMP ° C. | TIME, HRS | SUBSTITUTED ANTHRACENE CONVERSION TO OLEFIN ADDUCT, % | COMPOSITION OF GAS FROM ADDUCT DISSOCIATION, VOLUME % | | |
|---|---|---|---|---|---|---|
| | | | | ETHYLENE | PROPYLENE | OTHER[a] |
| 9 | 280 | 7 | 9-Methylanthracene 79.2 | 91.9 | 8.1 | 0.03[a] |
| 10 | 255 | 6 | 2-Ethylanthracene 50.9 | 88.3 | 11.3 | 0.4[a] |
| 11 | 255 | 6 | 9-Ethylanthracene 50.5 | 90.7 | 8.5 | 0.8[a] |
| 12 | 255 | 6 | 9-Isopropylanthracene 73.5 | 91.1 | 8.4 | 0.5[a] |
| 13 | 255 | 6 | 2-Methylanthracene 40.4 | 86.0 | 14.0 | 0.01[a] |
| 14 | 255 | 6 | 9-Cyanoanthracene 31.8 | 88.1 | 11.9 | 0.01[a] |
| 15 | 255 | 6 | 9-Acetylanthracene 40 | 84.0 | 9.3 | 6.7[b] |

[a]Contaminants inadvertently introduced from the experimental procedures.
[b]Mainly carbon monoxide from partial decomposition of 9-acetylanthracene.

What we claim is:

1. A process for treating a feedstock comprising olefins having an average carbon number ranging from 2–3.5, and non-olefinic compounds comprising at least one component that is reactive towards dienes, said process comprising:
   a) contacting a gaseous feedstock with a linear polyaromatic compound in a reaction zone under conditions effective to form a reaction mixture comprising linear polyaromatic compound-olefin adducts and unreacted gaseous feedstock, wherein said gaseous feedstock is selected from the group consisting of a stream derived from an olefins pyrolysis furnace; a stream derived from a catalytic cracker; a stream derived from a coker; a stream derived from a steam cracker; a stream derived from a wax cracker; a stream derived from a refinery thermal cracker using a vacuum flasher bottoms as the feed; a stream derived from a mixture of $C_4$ hydrocarbons or less cut of a fractionation column fed by the product of a catalytic cracker; a stream derived by removal of light ends in a Fisher-Tropsch stream; a stream used to feed a $C_2$ splitter; a stream used to feed a $C_3$ splitter; a refinery grade propylene stream; and a chemical grade propylene stream;
   b) separating the olefin adducts from the unreacted gaseous feedstock; and
   c) dissociating the olefin adducts to form linear polyaromatic compounds and an olefin enriched composition comprising ethylene, propylene, or mixtures thereof;
whereby the concentration of at least one of the olefins in said olefin enriched composition is enriched over the concentration of the corresponding olefin in the feedstock.

2. The process of claim 1, wherein the feedstock is contacted with a linear polyaromatic compound at a temperature ranging from 200° C. to about 320° C.

3. The process of claim 2, wherein the feedstock is contacted with linear polyaromatic compound at a temperature ranging from about 250° C. to about 280° C.

4. The process of claim 1, wherein the linear polyaromatic compound-olefin adduct is dissociated by heating the linear polyaromatic compound-olefin adduct to a temperature ranging from about 200° C. to 500° C.

5. The process of claim 4, wherein the linear polyaromatic compound-olefin adduct is heated to a temperature ranging from about 300° C. to 350° C.

6. The process of claim 1, wherein the feedstock comprises a stream derived by an olefins pyrolysis furnace.

7. The process of claim 1, wherein the feedstock comprises ethylene, ethane, hydrogen, and carbon dioxide.

8. A process for treating a feedstock comprising olefins having an average carbon number ranging from 2–3.5, and non-olefinic compounds, said process comprising the following steps:
   a) contacting a gaseous feedstock comprising methane, ethane, ethylene, propylene, carbon dioxide, carbon monoxide, hydrogen, and sulfur bearing compounds with a linear polyaromatic compound in a reaction zone under conditions effective to form a reaction mixture comprising linear polyaromatic compound-olefin adducts and unreacted gaseous feedstock;
   b) separating the olefin adducts from the unreacted gaseous feedstock; and
   c) dissociating the olefin adducts to form linear polyaromatic compounds and an olefin enriched composition comprising ethylene, propylene, or mixtures thereof;
whereby the concentration of at least one of the olefins in said olefin enriched composition is enriched over the concentration of the corresponding olefin in the feedstock.

9. The process of claim 8, wherein the feedstock comprises, by volume percentage bases on the volume of the feedstock, from 20–60% methane, 10–30% ethane, 5–35% ethylene, 0.5–20% propylene, 0.1–25% carbon dioxide, 0.5–10% carbon monoxide, 5–40% hydrogen, and from 0.0005–1% sulfur bearing compounds.

10. The process of claim 1, wherein the selectivity of the linear polyaromatic compound toward said olefins is 90% or more.

11. The process of claim 1, wherein the selectivity of the linear polyaromatic compound toward said olefins is 95% or more.

12. The process of claim 1, wherein the selectivity of the linear polyaromatic compound toward said olefins is 98% or more.

13. The process of claim 1, wherein the selectivity of the linear polyaromatic compound toward said olefins is 99% or more.

14. The process of claim 1, wherein the conversion of said olefins in the feedstock to olefin adducts is at least 30%, and the selectivity of the linear polyaromatic compound toward said olefins is 98% or more.

15. The process of claim 1, wherein the concentration of the olefin(s) in said olefin enriched composition is enriched by at least 100%.

16. The process of claim 1, wherein at least 95 vol. % of the olefin enriched composition comprises olefins.

17. The process of claim 1, wherein at least 98 vol. % of the olefin enriched composition comprises olefins.

18. A process for treating a feedstock comprising olefins having an average carbon number ranging from 2–3.5, and non-olefinic compounds comprising at least one component that is reactive toward dienes, said process comprising:
   a) contacting a gaseous feedstock with a linear polyaromatic compound in a reaction zone under conditions effective to form a reaction mixture comprising linear polyaromatic compound-olefin adducts and unreacted gaseous feedstock, wherein the amount of non-olefinic compounds in said gaseous feedstock ranges from 5 to 70 vol. % based on the weight of all ingredients in said gaseous feedstock;
   b) separating the olefin adducts from the unreacted gaseous feedstock; and
   c) dissociating the olefin adducts to form linear polyaromatic compounds and an olefin enriched composition comprising ethylene, propylene, or mixtures thereof;
whereby the concentration of at least one of the olefins in said olefin enriched composition is enriched over the concentration of the corresponding olefin in the feedstock.

19. The process of claim 18, wherein the amount of non-olefinic compounds in the feedstock ranges from 40 vol. % to 70 vol. %.

20. The process of claim 1, wherein the feedstock has an average carbon number ranging from 2–3.

21. The process of claim 1, wherein the concentration of non-olefinic compounds in the olefin enriched composition is reduced by at least 95% over the concentration of non-olefinic compounds in the feedstock.

22. The process of claim 21, wherein the concentration of non-olefinic compounds in the olefin enriched composition is reduced by at least 98% over the concentration of non-olefinic compounds in the feedstock.

23. The process of claim 1, wherein the linear polyaromatic compound comprises anthracene and/or benzanthracene.

24. The process of claim 1, wherein the linear polyaromatic compound comprises anthracene having a purity of 75% or more anthracene.

25. The process of claim 1, wherein step a) is conducted in a bubble column or in a spray column.

26. The process of claim 1, wherein the feedstock is introduced to a reaction vessel in step a) as a gas, and the linear polyaromatic compound is introduced into the reaction vessel as a liquid.

27. The process of claim 1, wherein the feedstock comprises a stream derived from a catalytic cracker.

28. The process of claim 1, wherein the feedstock comprises a stream derived from a coker.

29. The process of claim 1, wherein the feedstock comprises a stream derived from a steam cracker.

30. The process of claim 1, wherein the feedstock comprises a stream derived from a wax cracker.

31. The process of claim 1, wherein the feedstock comprises a stream derived from a refinery thermal cracker using a vacuum flasher bottoms as the feed.

32. The process of claim 1, wherein the feedstock comprises a stream derived from a mixture of $C_4$ hydrocarbons or less cut of a fractionation column fed by the product of a catalytic cracker.

33. The process of claim 1, wherein the feedstock comprises a stream comprising light ends derived by removal of light ends in a Fisher-Tropsch stream.

34. A process for treating a feedstock comprising olefins having an average carbon number ranging from 2–3.5, and non-olefinic compounds comprising at least one component that is reactive toward dienes, said process comprising:
   a) contacting a gaseous feedstock comprising a stream used to feed a $C_2$ splitter with a linear polyaromatic compound in a reaction zone under conditions effective to form a reaction mixture comprising linear polyaromatic compound-olefin adducts and unreacted gaseous feedstock;
   b) separating the olefin adducts from the unreacted gaseous feedstock; and
   c) dissociating the olefin adducts to form linear polyaromatic compounds and an olefin enriched composition comprising ethylene, propylene, or mixtures thereof;
whereby the concentration of at least one of the olefins in said olefin enriched composition is enriched over the concentration of the corresponding olefin in the feedstock.

35. The process of claim 34, wherein the feedstock contains at least 90wt. % of $C_2$ compounds.

36. The process of claim 35, wherein the feedstock contains at least 95wt. % $C_2$ compounds.

37. A process for treating a feedstock comprising olefins having an average carbon number ranging from 2–3.5, and non-olefinic compounds comprising at least one component that is reactive toward dienes, said process comprising:
   a) contacting a gaseous feedstock comprising a stream used to feed a $C_3$ splitter with a linear polyaromatic compound in a reaction zone under conditions effective to form a reaction mixture comprising linear polyaromatic compound-olefin adducts and unreacted gaseous feedstock;
   b) separating the olefin adducts from the unreacted gaseous feedstock; and
   c) dissociating the olefin adducts to form linear polyaromatic compounds and an olefin enriched composition comprising ethylene, propylene, or mixtures thereof,
whereby the concentration of at least one of the olefins in said olefin enriched composition is enriched over the concentration of the corresponding olefin in the feedstock.

38. The process of claim 37, wherein the feedstock comprises a refinery grade propylene stream.

39. The process of claim 38, wherein the feedstock comprises a chemical grade propylene stream.

40. A process for separating olefins from non-olefinic byproducts in an industrial gas stream, said process comprising:
   a) contacting said industrial gas stream comprising said olefins with one or more linear polyaromatic compounds in a reaction zone under conditions effective to form a reaction mixture comprising unreacted gaseous feedstock and adducts comprising said one or more linear polyaromatic compounds and said olefins, said industrial gas stream comprising at least one component that is reactive toward dienes;
   b) separating said adducts from said unreacted gaseous feedstock; and
   c) dissociating said adducts to form said one or more linear polyaromatic compounds and an olefin enriched composition comprising said olefins;
whereby the concentration of at least one of said olefins in said olefin enriched composition is enriched over the concentration of the corresponding olefin in said industrial gas stream.

41. A process for separating olefins from non-olefinic byproducts in an industrial gas stream, said process comprising:
   a) contacting the industrial gas stream comprising olefins having an average carbon number ranging from 2–3.5 with one or more linear polyaromatic compounds in a reaction zone under conditions effective to form a reaction mixture comprising linear polyaromatic compound-olefin adducts and unreacted gaseous feedstock, said industrial gas stream comprising at least one component that is reactive toward dienes;
   b) separating the olefin adducts from the unreacted gaseous feedstock; and
   c) dissociating the olefin adducts to form said linear polyaromatic compounds and an olefin enriched composition comprising said olefins having an average carbon number ranging from 2–3.5;
whereby the concentration of at least one of the olefins in said olefin enriched composition is enriched over the concentration of the corresponding olefin in said industrial gas stream.

42. The process of claim 41 wherein said olefins having an average carbon number ranging from 2–3.5 are selected from the group consisting of ethylene, propylene, and mixtures thereof.

43. The process of claim 41 wherein said industrial gas stream is contacted with a linear polyaromatic compound at a temperature ranging from 200° C. to about 320° C.

44. The process of claim 41 wherein said linear polyaromatic compound-olefin adduct is dissociated by heating said adduct to a temperature ranging from about 200° C. to 500° C.

45. The process of claim 41 wherein the selectivity of said linear polyaromatic compound toward said olefins is 90% or more.

46. The process of claim 41 wherein the selectivity of said linear polyaromatic compound toward said olefins is 95% or more.

47. The process of claim 41 wherein the selectivity of said linear polyaromatic compound toward said olefins is 98% or more.

48. The process of claim 41 wherein the selectivity of said linear polyaromatic compound toward said olefins is 99% or more.

49. The process of claim 41 wherein the conversion of said olefins to said adducts is at least 30%, and the selectivity of said linear polyaromatic compound toward said olefins is 98% or more.

50. The process of claim 41 wherein the concentration of said olefin(s) in said olefin enriched composition is enriched by at least 100%.

51. The process of claim 41 wherein at least 95 vol. % of the olefin enriched composition comprises olefins.

52. The process of claim 41 wherein at least 98 vol. % of the olefin enriched composition comprises olefins.

53. The process of claim 41 wherein the concentration of non-olefinic compounds in said olefin enriched composition is reduced by at least 95% over the concentration of non-olefinic compounds in said industrial gas stream.

54. The process of claim 41 wherein the concentration of non-olefinic compounds in said olefin enriched composition is reduced by at least 98% over the concentration of non-olefinic compounds in said industrial gas stream.

55. The process of claim 41 wherein said linear polyaromatic compound comprises anthracene and/or benzanthracene.

56. The process of claim 41 wherein said linear polyaromatic compound comprises anthracene having a purity of 75% or more anthracene.

57. The process of claim 41 wherein (a) is conducted in a bubble column or in a spray column.

58. The process of claim 41 wherein said industrial gas stream is introduced to a reaction vessel in (a) as a gas, and said linear polyaromatic compound is introduced into said reaction vessel as a liquid.

59. The process of claim 41 wherein the amount of non-olefinic compounds in said industrial gas stream feedstock ranges from 5 to 70 vol. % based on the weight of all ingredients said industrial gas stream.

60. The process of claim 41 wherein the amount of non-olefinic compounds in said industrial gas stream ranges from 40 vol. % to 70 vol. %.

61. A process for treating a feedstock comprising olefins having an average carbon number ranging from 2–3.5, and non-olefinic compounds comprising at least one component that is reactive toward aliphatic unsaturated carbon-carbon bonds, said process comprising the following steps:
   a) contacting a gaseous feedstock with a linear polyaromatic compound in a reaction zone under conditions effective to form a reaction mixture comprising linear polyaromatic compound-olefin adducts and unreacted gaseous feedstock;
   b) separating the olefin adducts from the unreacted gaseous feedstock; and
   c) dissociating the olefin adducts to form linear polyaromatic compounds and an olefin enriched composition comprising ethylene, propylene, or mixtures thereof;
whereby the concentration of at least one of the olefins in said olefin enriched composition is enriched over the concentration of the corresponding olefin in the feedstock.

62. The process of claim 61 wherein the linear polyaromatic compound comprises anthracene and/or benzanthracene.

63. The process of claim 61 wherein the linear polyaromatic compound comprises anthracene having a purity of 75% or more anthracene.

64. The process of claim 61 wherein step a) is conducted in a bubble column or in a spray column.

65. The process of claim 62 wherein step a) is conducted in a bubble column or in a spray column.

66. The process of claim 63 wherein step a) is conducted in a bubble column or in a spray column.

67. The process of claim 61 wherein the feedstock is introduced to a reaction vessel in step a) as a gas, and the linear polyaromatic compound is introduced into the reaction vessel as a liquid.

68. The process of claim 62 wherein the feedstock is introduced to a reaction vessel in step a) as a gas, and the linear polyaromatic compound is introduced into the reaction vessel as a liquid.

69. The process of claim 63 wherein the feedstock is introduced to a reaction vessel in step a) as a gas, and the linear polyaromatic compound is introduced into the reaction vessel as a liquid.

70. The process of claim 64 wherein the feedstock is introduced to a reaction vessel in step a) as a gas, and the linear polyaromatic compound is introduced into the reaction vessel as a liquid.

71. The process of claim 61 wherein the selectivity of the linear polyaromatic compound toward said olefins is 90% or more.

72. The process of claim 61 wherein the selectivity of the linear polyaromatic compound toward said olefins is 95% or more.

73. The process of claim 61 wherein the selectivity of the linear polyaromatic compound toward said olefins is 98% or more.

74. The process of claim 61 wherein the selectivity of the linear polyaromatic compound toward said olefins is 99% or more.

75. The process of claim 61 wherein the conversion of said olefins in the feedstock to olefin adducts is at least 30%, and the selectivity of the linear polyaromatic compound toward said olefins is 98% or more.

76. The process of claim 61 wherein the concentration of the olefin(s) in said olefin enriched composition is enriched by at least 100%.

77. The process of claim 61 wherein at least 95 vol. % of the olefin enriched composition comprises olefins.

78. The process of claim 61 wherein at least 98 vol. % of the olefin enriched composition comprises olefins.

79. The process of claim 61 wherein the amount of non-olefinic compounds in the feedstock ranges from 40 vol. % to 70 vol. %.

80. The process of claim 61 wherein the feedstock has an average carbon number ranging from 2–3.

81. The process of claim 61 wherein the concentration of non-olefinic compounds in the olefin enriched composition is reduced by at least 95% over the concentration of non-olefinic compounds in the feedstock.

82. The process of claim 61 wherein the concentration of non-olefinic compounds in the olefin enriched composition is reduced by at least 98% over the concentration of non-olefinic compounds in the feedstock.

83. A process for treating a feedstock comprising olefins having an average carbon number ranging from 2–3.5, and comprising at least one component reactive toward dienes, said process comprising the following steps:
   a) contacting a gaseous feedstock with a linear polyaromatic compound in a reaction zone under conditions effective to form a reaction mixture comprising linear polyaromatic compound-olefin adducts and unreacted gaseous feedstock;
   b) separating the olefin adducts from the unreacted gaseous feedstock; and
   c) dissociating the olefin adducts to form linear polyaromatic compounds and an olefin enriched composition comprising ethylene, propylene, or mixtures thereof;
whereby the concentration of at least one of the olefins in said olefin enriched composition is enriched over the concentration of the corresponding olefin in the feedstock.

84. The process of claim 83 wherein the feedstock is contacted with a linear polyaromatic compound at a temperature ranging from 200° C. to about 320° C.

85. The process of claim 83 wherein the feedstock is contacted with linear polyaromatic compound at a temperature ranging from about 250° C. to about 280° C.

86. The process of claim 83 wherein the linear polyaromatic compound-olefin adduct is dissociated by heating the linear polyaromatic compound-olefin adduct to a temperature ranging from about 200° C. to 500° C.

87. The process of claim 83 wherein the linear polyaromatic compound-olefin adduct is heated to a temperature ranging from about 300° C. to 350° C.

88. The process of claim 83 wherein the feedstock comprises a stream derived by an olefins pyrolysis furnace.

89. The process of claim 83 wherein the feedstock comprises ethylene, ethane, hydrogen, and carbon dioxide.

90. The process of claim 83 wherein the feedstock comprises, by volume percentage bases on the volume of the feedstock, from 20–60% methane, 10–30% ethane, 5–35% ethylene, 0.5–20% propylene, 0.1–25% carbon dioxide, 0.5–10% carbon monoxide, 5–40% hydrogen, and from 0.0005–1% sulfur bearing compounds.

91. The process of claim 83 wherein the selectivity of the linear polyaromatic compound toward said olefins is 90% or more.

92. The process of claim 83 wherein the selectivity of the linear polyaromatic compound toward said olefins is 95% or more.

93. The process of claim 83 wherein the selectivity of the linear polyaromatic compound toward said olefins is 98% or more.

94. The process of claim 83 wherein the selectivity of the linear polyaromatic compound toward said olefins is 99% or more.

95. The process of claim 83 wherein the conversion of said olefins in the feedstock to olefin adducts is at least 30%, and the selectivity of the linear polyaromatic compound toward said olefins is 98% or more.

96. The process of claim 83 wherein the concentration of the olefin(s) in said olefin enriched composition is enriched by at least 100%.

97. The process of claim 83 wherein at least 95 vol. % of the olefin enriched composition comprises olefins.

98. The process of claim 83 wherein at least 98 vol. % of the olefin enriched composition comprises olefins.

99. The process of claim 83 wherein the amount of non-olefinic compounds in the feedstock ranges from 40 vol. % to 70 vol. %.

100. The process of claim 83 wherein the feedstock has an average carbon number ranging from 2–3.

101. The process of claim 83 wherein the concentration of non-olefinic compounds in the olefin enriched composition is reduced by at least 95% over the concentration of non-olefinic compounds in the feedstock.

102. The process of claim 83 wherein the concentration of non-olefinic compounds in the olefin enriched composition is reduced by at least 98% over the concentration of non-olefinic compounds in the feedstock.

103. The process of claim 83 wherein the linear polyaromatic compound comprises anthracene and/or benzanthracene.

104. The process of claim 88 wherein the linear polyaromatic compound comprises anthracene and/or benzanthracene.

105. The process of claim 89 wherein the linear polyaromatic compound comprises anthracene and/or benzanthracene.

106. The process of claim 90 wherein the linear polyaromatic compound comprises anthracene and/or benzanthracene.

107. The process of claim 83 wherein the linear polyaromatic compound comprises anthracene having a purity of 75% or more anthracene.

108. The process of claim 88 wherein the linear polyaromatic compound comprises anthracene having a purity of 75% or more anthracene.

109. The process of claim 89 wherein the linear polyaromatic compound comprises anthracene having a purity of 75% or more anthracene.

110. The process of claim 90 wherein the linear polyaromatic compound comprises anthracene having a purity of 75% or more anthracene.

111. The process of claim 83 wherein step a) is conducted in a bubble column or in a spray column.

112. The process of claim wherein 83 the feedstock is introduced to a reaction vessel in step a) as a gas, and the linear polyaromatic compound is introduced into the reaction vessel as a liquid.

113. The process of claim 83 wherein the feedstock comprises a stream derived from a catalytic cracker.

114. The process of claim 83 wherein the feedstock comprises a stream derived from a coker.

115. The process of claim 83 wherein the feedstock comprises a stream derived from a steam cracker.

116. The process of claim 83 wherein the feedstock comprises a stream derived from a wax cracker.

117. The process of claim 83 wherein the feedstock comprises a stream derived from a refinery thermal cracker using a vacuum flasher bottoms as the feed.

118. The process of claim 83 wherein the feedstock comprises a stream derived from a mixture of $C_4$ hydrocarbons or less cut of a fractionation column fed by the product of a catalytic cracker.

119. The process of claim 83 wherein the feedstock comprises a stream comprising light ends derived by removal of light ends in a Fisher-Tropsch stream.

120. The process of claim 83 wherein the feedstock contains at least 90 wt. % of $C_2$ compounds.

121. The process of claim 83 wherein the feedstock contains at least 95 wt. % $C_2$ compounds.

122. The process of claim 113 wherein the linear polyaromatic compound comprises anthracene and/or benzanthracene.

123. The process of claim 114 wherein the linear polyaromatic compound comprises anthracene and/or benzanthracene.

124. The process of claim 115 wherein the linear polyaromatic compound comprises anthracene and/or benzanthracene.

125. The process of claim 116 wherein the linear polyaromatic compound comprises anthracene and/or benzanthracene.

126. The process of claim 117 wherein the linear polyaromatic compound comprises anthracene and/or benzanthracene.

127. The process of claim 118 wherein the linear polyaromatic compound comprises anthracene and/or benzanthracene.

128. The process of claim 119 wherein the linear polyaromatic compound comprises anthracene and/or benzanthracene.

129. The process of claim 113 wherein the linear polyaromatic compound comprises anthracene having a purity of 75% or more anthracene.

130. The process of claim 114 wherein the linear polyaromatic compound comprises anthracene having a purity of 75% or more anthracene.

131. The process of claim 115 wherein the linear polyaromatic compound comprises anthracene having a purity of 75% or more anthracene.

132. The process of claim 116 wherein the linear polyaromatic compound comprises anthracene having a purity of 75% or more anthracene.

133. The process of claim 117 wherein the linear polyaromatic compound comprises anthracene having a purity of 75% or more anthracene.

134. The process of claim 118 wherein the linear polyaromatic compound comprises anthracene having a purity of 75% or more anthracene.

135. The process of claim 119 wherein the linear polyaromatic compound comprises anthracene having a purity of 75% or more anthracene.

136. A process for treating a feedstock comprising olefins having an average carbon number ranging from 2–3.5, and non-olefinic compounds, said process comprising:
  a) contacting a gaseous feedstock with a linear polyaromatic compound in a reaction zone under conditions effective to form a reaction mixture comprising linear polyaromatic compound-olefin adducts and unreacted gaseous feedstock, wherein said gaseous feedstock is selected from the group consisting of a stream derived from an olefins pyrolysis furnace;-a stream derived from a catalytic cracker; a stream derived from a coker; a stream derived from a steam cracker; a stream derived from a wax cracker; a stream derived from a refinery thermal cracker using a vacuum flasher bottoms as the feed; a stream derived from a mixture of $C_4$ hydrocarbons or less cut of a fractionation column fed by the product of a catalytic cracker; a stream derived by removal of light ends in a Fisher-Tropsch stream; a stream used to feed a $C_2$ splitter; a stream used to feed a $C_3$ splitter; refinery grade and chemical grade propylene streams; and
  b) separating the olefin adducts from the unreacted gaseous feedstock; and
  c) dissociating the olefin adducts to form linear polyaromatic compounds and an olefin enriched composition comprising ethylene, propylene, or mixtures thereof;
whereby the concentration of at least one of the olefins in said olefin enriched composition is enriched over the concentration of the corresponding olefin in the feedstock.

137. A process for treating a feedstock comprising olefins having an average carbon number ranging from 2–3.5, and non-olefinic compounds comprising at least one component selected from the group consisting of carbon oxides, sulfur bearing compounds, and nitrogen bearing compounds, said process comprising:
  a) contacting a gaseous feedstock with a linear polyaromatic compound in a reaction zone under conditions effective to form a reaction mixture comprising linear polyaromatic compound-olefin adducts and unreacted gaseous feedstock, wherein the amount of non-olefinic compounds in said gaseous feedstock ranges is at least about 40 vol. % based on the weight of all ingredients in said gaseous feedstock;
  b) separating the olefin adducts from the unreacted gaseous feedstock; and
  c) dissociating the olefin adducts to form linear polyaromatic compounds and an olefin enriched composition comprising ethylene, propylene, or mixtures thereof;
whereby the concentration of at least one of the olefins in said olefin enriched composition is enriched over the concentration of the corresponding olefin in the feedstock.

138. The process of claim 137, wherein the linear polyaromatic compound comprises anthracene and/or benzanthracene.

139. A process for treating a feedstock comprising olefins having an average carbon number ranging from 2–3.5, and non-olefinic compounds comprising at least one component selected from the group consisting of carbon oxides, sulfur bearing compounds, and nitrogen bearing compounds, said process comprising:
  a) contacting a gaseous feedstock with a linear polyaromatic compound in a reaction zone under conditions effective to form a reaction mixture comprising linear polyaromatic compound-olefin adducts and unreacted gaseous feedstock, wherein said gaseous feedstock comprises light ends derived by removal of light ends in a Fisher-Tropsch stream;
  b) separating the olefin adducts from the unreacted gaseous feedstock; and
  c) dissociating the olefin adducts to form linear polyaromatic compounds and an olefin enriched composition comprising ethylene, propylene, or mixtures thereof;
whereby the concentration of at least one of the olefins in said olefin enriched composition is enriched over the concentration of the corresponding olefin in the feedstock.

140. The process of claim 139, wherein the linear polyaromatic compound comprises anthracene and/or benzanthracene.

141. A process for separating olefins from non-olefinic byproducts in an industrial gas stream, said process comprising:
  a) contacting said industrial gas stream comprising said olefins with one or more linear polyaromatic compounds in a reaction zone under conditions effective to form a reaction mixture comprising unreacted gaseous feedstock and adducts comprising said one or more linear polyaromatic compounds and said olefins, said industrial gas stream comprising at least one component selected from the group consisting of carbon oxides, sulfur bearing compounds, and nitrogen bearing compounds;
  b) separating said adducts from said unreacted gaseous feedstock; and
  c) dissociating said adducts to form said one or more linear polyaromatic compounds and an olefin enriched composition comprising said olefins;
whereby the concentration of at least one of said olefins in said olefin enriched composition is enriched over the concentration of the corresponding olefin in said industrial gas stream.

142. The process of claim 141 wherein said olefins having an average carbon number ranging from 2–3.5 are selected from the group consisting of ethylene, propylene, and mixtures thereof.

143. The process of claim 141 wherein said linear polyaromatic compound comprises anthracene and/or benzanthracene.

144. A process for treating a feedstock comprising olefins having an average carbon number ranging from 2–3.5, and non-olefinic compounds, said process comprising:
  a) contacting a gaseous feedstock with a linear polyaromatic compound in a reaction zone under conditions effective to form a reaction mixture comprising linear polyaromatic compound-olefin adducts and unreacted gaseous feedstock, wherein said gaseous feedstock comprises light ends derived by removal of light ends in a Fisher-Tropsch stream;

b) separating the olefin adducts from the unreacted gaseous feedstock; and c) dissociating the olefin adducts to form linear polyaromatic compounds and an olefin enriched composition comprising ethylene, propylene, or mixtures thereof; whereby the concentration of at least one of the olefins in said olefin enriched composition is enriched over the concentration of the corresponding olefin in the feedstock.

145. The process of claim 144 wherein said linear polyaromatic compound comprises anthracene and/or benzanthracene.

* * * * *